(12) United States Patent
Wick

(10) Patent No.: US 8,524,482 B1
(45) Date of Patent: Sep. 3, 2013

(54) METHOD AND SYSTEM FOR SAMPLING AND SEPARATING SUBMICRON-SIZED PARTICLES BASED ON DENSITY AND OR SIZE TO DETECT THE PRESENCE OF A PARTICULAR AGENT

(75) Inventor: Charles H. Wick, Darlington, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 522 days.

(21) Appl. No.: 12/435,477

(22) Filed: May 5, 2009

(51) Int. Cl.
*C12N 7/02* (2006.01)
*C12Q 1/70* (2006.01)
*A61K 39/00* (2006.01)

(52) U.S. Cl.
USPC .............................. 435/239; 435/5; 424/184.1

(58) Field of Classification Search
None
See application file for complete search history.

(56) References Cited

PUBLICATIONS

Kuzmanovic et al., Bacteriophage MS2: Molecular Weight and Spatial Distribution of the Protein and RNA Components by Small-Angle Neutron Scattering and Virus Counting, 2003, Structure, vol. 11, pp. 1339-1348.*

Bacher et al., Charge-reduced nano electrospray ionization combined with differential mobility analysis of peptides, proteins, glycoproteins, noncovalent protein complexes and viruses, 2001, Journal of Mass Spectrometry, vol. 36, pp. 1038-1052.*

Johnson et al., Characterization of vaccinia virus particles using microscale silicon cantilever resonators and atomic force microscopy, 2006, Sensors and Actuators B, vol. 115, pp. 189-197.*

* cited by examiner

*Primary Examiner* — Benjamin P Blumel
(74) *Attorney, Agent, or Firm* — Ulysses John Biffoni

(57) ABSTRACT

A system for sampling and separating submicron-sized particles to detect the presence of an agent such as viruses in an environmental sample, which includes collecting means for collecting a sample suspected of containing submicron-sized particles from the environment, size separation means receiving the submicron-sized particles from the collecting means for separating the submicron-sized particles based on size into at least one size range, and a microscale particle counter adapted for counting the size separated submicron-sized particles received from the size separation means. The particle counter includes at least one cantilever each corresponding to submicron-sized particles of a particular size range, wherein the cantilever is deflectable from a first to a second position to permit passage of the submicron-sized particle therethrough, and wherein the corresponding deflection of the cantilever generates a count signal.

12 Claims, 8 Drawing Sheets

Figure 1:
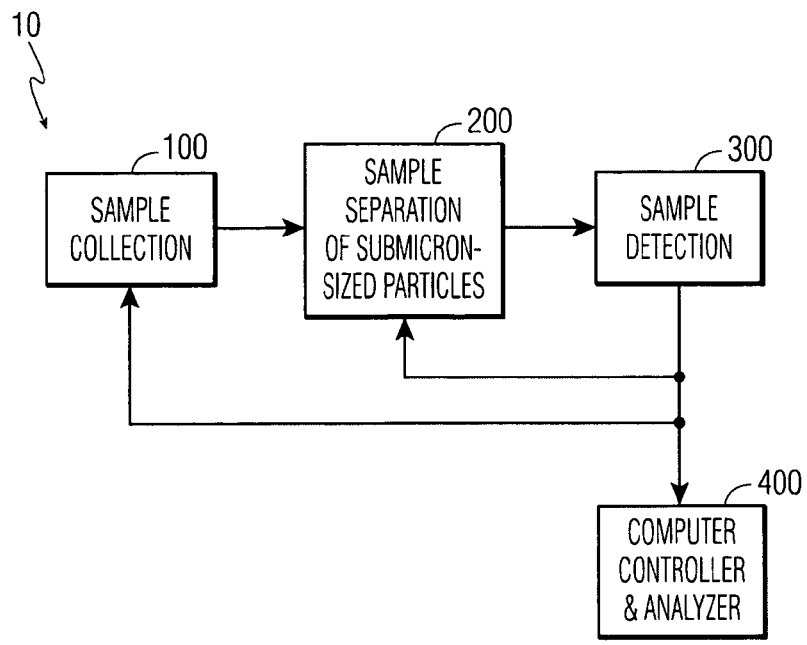

| LEGEND | VIRUS FAMILY | RANGE OF DENSITY, SIZE | PREFERRED RANGE OF DENSITY, SIZE |
|---|---|---|---|
| B | ADENOVIRIDAE | 1.30-1.39, 67-115 | 1.32-1.35, 80-110 |
| C | ARENAVIRIDAE | 1.18-1.25, 45 300 [1.27-1.36, 40 290] | 1.19-1.24, 50-150 |
| D | ASTROVIRIDAE | 1.35-1.44, 26-32 | 1.35-1.40, 27-31 |
| E | CALICIVIRIDAE | 1.32-1.45, 28-40 | 1.33-1.40, 29-39 |
| F | CORONAVIRIDAE | 1.18-1.26, 80-170 [1.25-1.33, 100-160] | 1.23-1.25, 120-160 |
| G | FILOVIRIDAE | 1.30-1.40, 75-400 [1.32-1.39, 70-390] | 1.31-1.34, 80-230 |
| H | HEPADNAVIRIDAE | 1.23-1.30, 30-45 [1.33-1.38, 24-40] | 1.24-1.26, 34-42 |
| I | HERPESVIRIDAE | 1.19-1.33, 90-200 [1.25-1.35, 90-180] | 1.20-1.30, 100-180 |
| J | ORTHOMYXOVIRIDAE | 1.18-1.26, 75-125 [1.25-1.34, 65-110] | 1.19-1.26, 80-120 |
| K | PAPOVAVIRIDAE | 1.19-1.36, 35-57 | 1.31-1.34, 40-55 and 1.19-1.24, 37-42 |
| L | PARAMYXOVIRIDAE | 1.18-1.27, 100-300 [1.25-1.33, 90-280] | 1.18-1.26, 130-200 |
| M | RETROVIRIDAE | 1.15-1.24, 70-120 [1.24-1.29, 70-95] | 1.17-1.23, 80-100 |
| N | FLAVIVIRIDAE | 1.14-1.28, 30-65 [1.25-1.32, 30-55] | 1.20-1.26, 40-60 |
| O | PARVOVIRIDAE | 1.38-1.45, 17-27 | 1.38-1.42, 18-26 |
| P | PICORNAVIRIDAE | 1.30-1.46, 20-30 | 1.31-1.44, 22-30 |
| Q | POXVIRIDAE | 1.28-1.35, 140-370 [1.29-1.38, 130-360] | 1.29-1.33, 150-350 |
| R | TOGAVIRIDAE | 1.17-1.27, 60-85 [1.24-1.33, 58-70] | 1.19-1.25, 65-80 |
| S | BUNYAVIRIDAE | 1.15-1.24, 80-130 [1.25-1.30, 70-110] | 1.19-1.22, 80-120 |
| T | REOVIRIDAE | 1.35-1.43, 55-85 | 1.36-1.39, 65-85 |
| U | RHABDOVIRIDAE | 1.17-1.23, 45-300 [1.20-1.27, 40-290] | 1.18-1.21, 50-220 |

FIG. 8

METHOD AND SYSTEM FOR SAMPLING AND SEPARATING SUBMICRON-SIZED PARTICLES BASED ON DENSITY AND OR SIZE TO DETECT THE PRESENCE OF A PARTICULAR AGENT

GOVERNMENT INTEREST

The invention described herein may be manufactured, used and licensed by or for the U.S. Government. The present invention is related to U.S. Pat. Nos. 6,051,189, 6,485,686, 6,491,872, and 7,250,138, each assigned to the United States Government, and is incorporated herein by reference to the extent they do not conflict herewith.

FIELD OF THE INVENTION

The present invention relates to fluid sample testing, and more particularly to system and methods for sampling and separating submicron-sized particles based on density and/or size to detect the presence of a particular agent such as, for example, viruses in an environmental sample.

BACKGROUND OF THE INVENTION

Viruses are considered to be among the smallest particles known to man. Viruses are about a hundred times smaller than bacteria, and make up a group of submicroscopic infectious agents that are unable to grow or reproduce outside of a host cell. Certain viruses can cause harm or death in their infected host. Because of their small size, viruses are extremely difficult to detect and characterize. Detection and identification of viruses have been a complicated process in any given environment, especially under combat conditions where pathogenic viruses can be used in biological warfare (BW). Devices are needed which enable detection of remote dispersal of BW agents in a field environment for early warning capabilities.

Rapid detection and warning are essential for providing protection of civilians and soldiers from a BW attack. Previous known methods utilizing biochemical reagents such as multiplex polymerase chain reaction (PCR), low-stringency nucleic acid hybridization and polyclonal antibodies, are often impractical in the field. Polymerase chain reaction is used to detect the presence of a specific genetic sequence, while antibody-based methods detect specific antigens. Both methods work well when testing for known viruses for which genetic primers or antibodies have been developed. Such methods are expensive and typically require time and intensive labor for proper implementation, while providing limited detection capabilities restricted to only certain BW agents.

Biochemical reagent based methods are often hampered by high frequency of false positives under both laboratory and field conditions. The PCR and antibody-based methods require a single test per virus, and often one test per strain of virus. This limits their capacity to monitor and screen all strains of pathogenic viruses in a cost effective manner. Furthermore, these methods cannot actively adapt to rapid mutation of viruses, or emergence of new, unknown viruses, thus failing to provide broad-detection of all viruses regardless of identity, known or unknown, sequenced or un-sequenced.

As set forth in U.S. Pat. Nos. 6,051,189, 6,485,686, 6,491,872, and 7,250,138, assigned to the U.S. Government, viruses may be detected in an environment without reliance on biochemical means by capitalizing on the physical properties of size and density. Suspected viruses can be quickly extracted and detected from an environmental sample through isolation of particles based on sizes and densities, which closely match with those of viral agents. Purification processes can also be used to further concentrate suspected particles to the extent necessary to overcome background contamination. In this manner, reliable and rapid detection of potentially dangerous viruses can be effectively achieved.

This is accomplished through the use of centrifugal techniques, which sorts submicron-sized particles according to density, and differential mobility analysis, which sorts submicron-sized particles according to size. Once isolated and sorted, particles with sizes as small as 2 to 3 nanometers can be detected and counted using a condensation nucleus counter. In this device, a liquid, such as butyl alcohol, is condensed on the particles so they grow to a diameter of about a micrometer. They are then large enough to scatter an appreciable amount of light. By passing these particles through a beam of light, flashes of light are produced. The resulting flashes can be detected and counted to determine the concentration of particles in the flow from the differential mobility analyzer.

In this manner, the resulting particles having a particular density and size matching a particular agent such as viruses are effectively isolated and detected in the sample. The strength of such technology is the capability to detect any virus in a single relatively straightforward test, while providing useful quantitative results. Such systems, however, remain large and bulky and require a substantial amount of time to implement. In addition, the use of condensation nucleus counters often adversely alters the extracted particles in a manner, which render them of limited usefulness for further testing.

Accordingly, there is a need to develop a system and method for sampling and separating submicron-sized particles based on density and/or size to detect the presence of a particular agent such as, for example, viruses in an environmental sample, that is substantially compact, lightweight, cost effective and simple to implement, while enhancing accuracy and reducing false positives. There is a need to develop a system or method for detecting the presence of a particular agent in the environment that enhances constant real-time monitoring with minimal preparation and setup. There is a further need to develop a system and method that does not adversely affect or alter the particular agent upon isolation and detection, in a manner, which hinders further testing or confirmation.

SUMMARY OF THE INVENTION

The present invention relates generally to a system and method for sampling and separating submicron-sized particles based on density and/or size to detect the presence of a particular agent such as, for example, viruses, in an environmental sample. Generally, the system of the present invention includes collecting means for collecting a sample from the environment, size separation means receiving the sample from the collecting means for separating or isolating submicron-sized particles in the sample based on size, and detection means for detecting particular agents which may be present among the isolated submicron-sized particles. The system and method of the present invention is capable of sampling and separating submicron-sized particles in the size range of from about 5 to 1000 nanometers. The system of the present invention can further include density separation means receiving the sample from the collecting means for separating or isolating the submicron-sized particles based on density as a function of the density gradient. Automated control means can be utilized to control the flow of the sample through the system.

The size separation means generally includes a microscale compact field charger for placing a surface charge on the submicron-sized particles, and a microscale differential mobility classifier for separating the submicron-sized particles based on size as a function of the electrical mobility. The size separation means can further include a filter apparatus for filtering the environmental sample to purify and concentrate the submicron-sized particles. The detection means generally includes a microscale particle counter adapted for counting the size separated submicron-sized particles received from the size separation means.

The collecting means include a collector, which is adapted to collect fluid samples including liquid and air samples. The collector includes a liquid scrubber for scrubbing a fluid sample of aerosol and gaseous materials containing the submicron-sized particles. The collecting means is intended to collect a sample containing submicron-sized particles, which may include viruses, prions, macromolecules, proteins and satellites, viral subunits, viral cores of delipidated viruses, plant viruses, and other chemical and biological materials such as nanometer size portions of bacteria.

The method for detecting the presence of submicron-sized particles in a sample taken from the environment, includes the steps of collecting a sample suspected of containing submicron-sized particles from the environment, separating by size the submicron-sized particles in the sample, and counting the size separated submicron-sized particles via a microscale particle counter comprising at least one cantilever each corresponding to submicron-sized particles of a particular size range, the cantilever being deflectable from a first to a second position to permit passage of the submicron-sized particle therethrough, wherein the corresponding deflection of the cantilever generates a count signal.

In one aspect of the present invention, there is provided a system for sampling and separating submicron-sized particles to detect the presence of an agent such as viruses in an environmental sample, where the system includes:

collecting means for collecting a sample suspected of containing submicron-sized particles from the environment;

size separation means receiving the submicron-sized particles from the collecting means for separating the submicron-sized particles based on size into at least one size range; and a microscale particle counter adapted for counting the size separated submicron-sized particles received from the size separation means, the particle counter comprising at least one cantilever each corresponding to submicron-sized particles of a particular size range, the cantilever being deflectable from a first to a second position to permit passage of the submicron-sized particle therethrough, wherein the corresponding deflection of the cantilever generates a count signal.

In another aspect of the present invention, there is provided a method for sampling and separating submicron-sized particles to detect the presence of an agent such as viruses in an environmental sample, where the method include the steps of:

collecting a sample suspected of containing submicron-sized particles from the environment;

size separating the submicron-sized particles in the sample based on size; and counting the separated submicron-sized particles according to size via a microscale particle counter comprising at least one cantilever each corresponding to submicron-sized particles of a particular size range, the cantilever being deflectable from a first to a second position to permit passage of the submicron-sized particle therethrough, wherein the corresponding deflection of the cantilever generates a count signal.

Accordingly, an object of the present invention is to detect known and unknown or submicron-sized particles.

Another object of the present invention is to provide a method and apparatus for the efficient and rapid detection and identification of submicron-sized particles based on the physical characteristics of the particles.

A further object of the present invention is to provide an automated system for the detection and identification of submicron-sized particles.

These, together with still other objects of the invention, along with the various features, which characterize the invention, are pointed out with particularity in the appended claims.

BRIEF DESCRIPTION OF THE DRAWINGS

The following drawings are illustrative of embodiments of the present invention and are not intended to limit the invention as encompassed by the claims forming part of the application, wherein like items are identified by the same reference designations:

FIG. 1 is general block diagram showing key components of a system for sampling and separating submicron-sized particles based on density and/or size to detect the presence of a particular agent in accordance with the present invention;

FIG. 2 is a block diagram showing elements forming part of the sample separation and detection components of the system in accordance with one embodiment of the present invention;

FIG. 3 shows a graph of extrinsic charged fraction versus particle size to illustrate the charging efficiency of a microscale compact field charger in accordance with the present invention;

FIG. 4 is a graph providing characteristic cutoff curves of a microscale differential mobility classifier displaying the percent penetration versus applied voltage for various particle sizes in accordance with the present invention;

FIG. 5 is a graph plotting cutoff curve slope versus particle electrical mobility, $Z_p$, for the differential mobility classifier in accordance with the present invention;

FIG. 6 is a schematic illustration of the system in accordance with the present invention;

FIG. 7 is a plot of the virus window showing the densities and sedimentation coefficients for viruses pathogenic to man;

FIG. 8 is a table providing the densities (g/ml) and size (nm) for known viral families containing species pathogenic to man;

FIG. 9 is a cross-sectional representation of a microscale differential mobility classifier for one embodiment of the present invention; and FIG. 10 is a cross-sectional representation of the differential mobility classifier shown in operative association with microscale particle counters for a further embodiment of the present invention.

DETAILED DESCRIPTION OF THE INVENTION

The present invention relates generally to a system and method for sampling and separating submicron-sized particles based on density and/or size to detect the presence of a particular agent such as, for example, viruses, in an environmental sample. In particular, the method and system allows for the collection, concentration, purification and detection of viruses that are pathogenic to humans. Generally, the system of the present invention includes collecting means for collecting a sample from the environment, size separation means receiving the sample from the collecting means for separating or isolating submicron-sized particles in the sample based on size, and detection means for detecting particular agents which may be present among the isolated submicron-sized particles. The system and method of the present invention is capable of sampling and separating submicron-sized particles in the size range of from about 5 to 1000 nanometers.

The system of the present invention can further include density separation means receiving the sample from the collecting means for separating or isolating the submicron-sized particles based on density as a function of the density gradient. Automated control means can be utilized to control the flow of the sample through the system.

The size separation means generally includes a microscale compact field charger for placing a surface charge on the submicron-sized particles, and a microscale differential mobility classifier for separating the submicron-sized particles based on size as a function of the electrical mobility. The size separation means can further include a filter apparatus for filtering the environmental sample to purify and concentrate the submicron-sized particles. The detection means generally includes a microscale particle counter adapted for counting the size separated submicron-sized particles received from the size separation means. The incorporation of the microscale compact field charger, microscale differential mobility classifier and microscale particle counter of the present invention greatly reduces the size and weight of the present system, and lessens the time for implementing the detection process.

In one embodiment of the present invention, there is provided a system for sampling and separating submicron-sized particles to detect the presence of an agent such as viruses in an environmental sample. The system comprises collecting means for collecting a sample suspected of containing submicron-sized particles from the environment, size separation means receiving the submicron-sized particles from the collecting means for separating the submicron-sized particles based on size into at least one size range, and a microscale particle counter. The microscale particle counter is adapted for counting the size separated submicron-sized particles received from the size separation means. The microscale particle counter comprises at least one cantilever each corresponding to submicron-sized particles of a particular size range. The cantilever is configured to be deflectable from a first to a second position to permit passage of the submicron-sized particle therethrough, wherein the corresponding deflection of the cantilever generates a count signal.

As used herein, the term "microscale" is intended to refer generally to components on the scale of from about 1 to 100 micrometers in size, and devices, generally at least 20 micrometers, including, but not limited to, microelectromechanical systems (MEMS). Such microscale devices can be fabricated using modified semiconductor fabrication technologies, including, but not limited to, molding and plating, wet etching (KOH, TMAH), dry etching such as reactive ion etching (RIE) and deep reactive ion etching (DRIE), xenon difluoride etching, electro discharge machining (EDM), and other technologies capable of manufacturing very small devices as known in the art.

With reference to FIG. 1, there is shown a system identified by reference numeral 10 in accordance with one embodiment of the present invention. The system 10 includes generally a sample collection section 100 adapted for collecting and processing a sample containing submicron-sized particles from an environment, a sample separation section 200 adapted for receiving the sample from the sample collection section 100 to separate the submicron-sized particles based on physical characteristics such as size and density, and a sample detection section 300 adapted for receiving the separated submicron-sized particles corresponding to the size and/or density of particular agents of interest from the sample separation section to detect the presence of the particular agents of interest. The system 10 further includes a computer controller and analyzer 400 to provide automated control of the flow of sample and implement the data analysis collected from the sample detection section 300.

Figure 2:
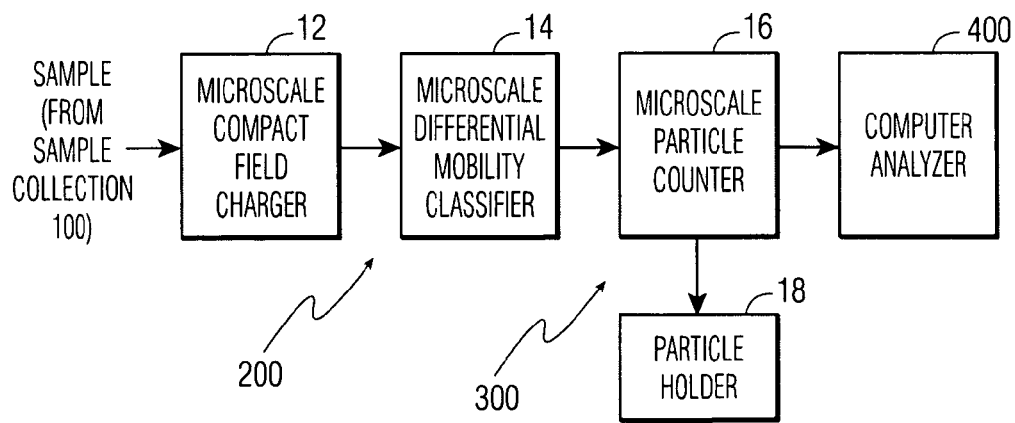
Figure 3:
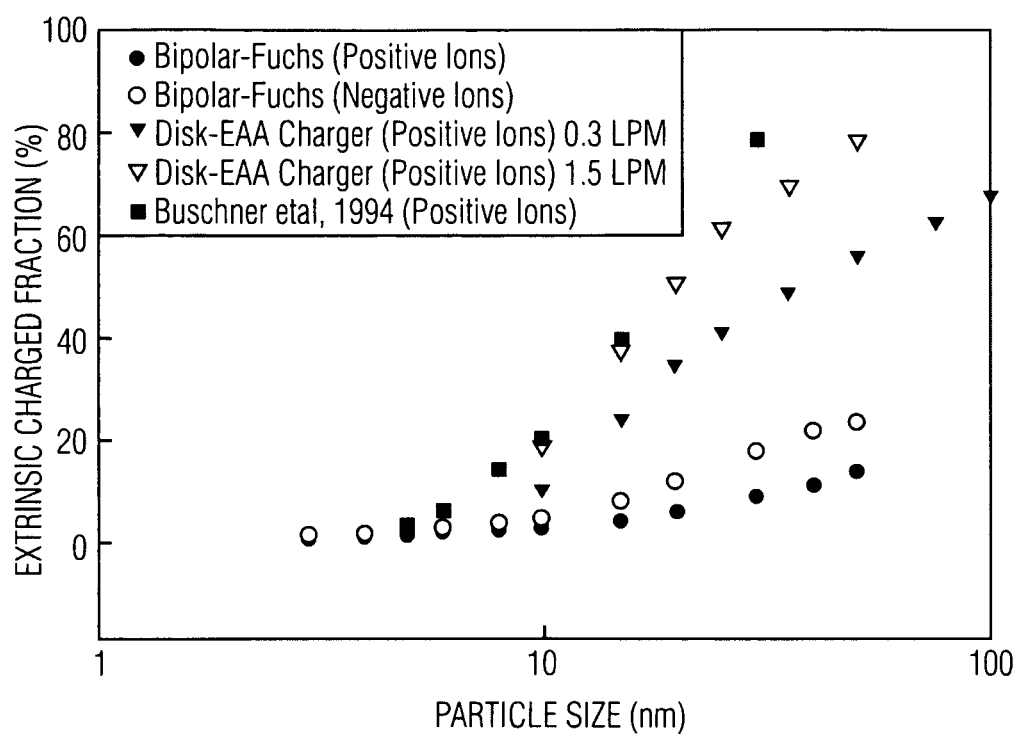

Referring to FIG. 2, the sample separation section 200 includes a microscale compact field charger or unipolar aerosol charger 12 adapted for placing a charge on the submicron-sized particles. Referring to FIG. 3, the charging efficiency of the compact field charger 12 (identified as Disk-EAA charger) is shown. A ten-fold increase in efficiency is achieved relative to isotope diffusion charging (i.e., Bipolar-Fuchs). Advances in materials and geometry of the discharge electrodes allow the microscale compact field charger 12 to operate at modest voltages of about 40V max. A suitable example of the microscale compact field charger 12 is a corona-discharge-based unipolar mini-charger or a unipolar corona discharge ionizer.

Referring back to FIG. 2, the sample separation section 200 further includes a microscale differential mobility classifier 14 adapted for receiving the charged submicron-sized particles from the compact field charger 12 and separating the submicron-sized particles based on size as a function of the electrical mobility as will be further discussed hereinafter. The differential mobility classifier 14 can be tuned to a specific size range, with the collected sample material representing a portion of the total particle population.

Figure 4:
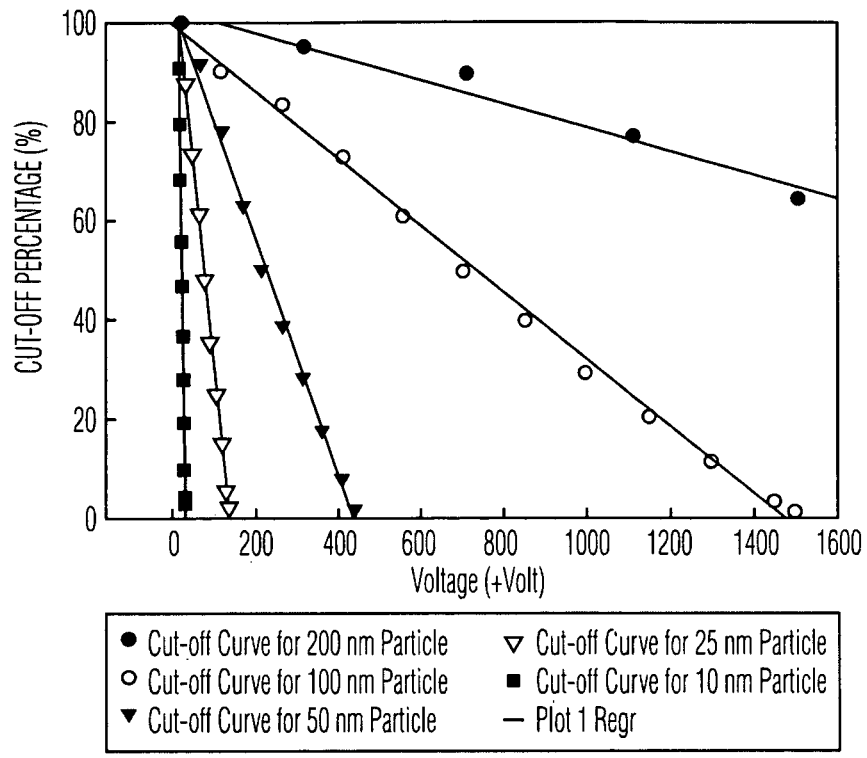
Figure 5:
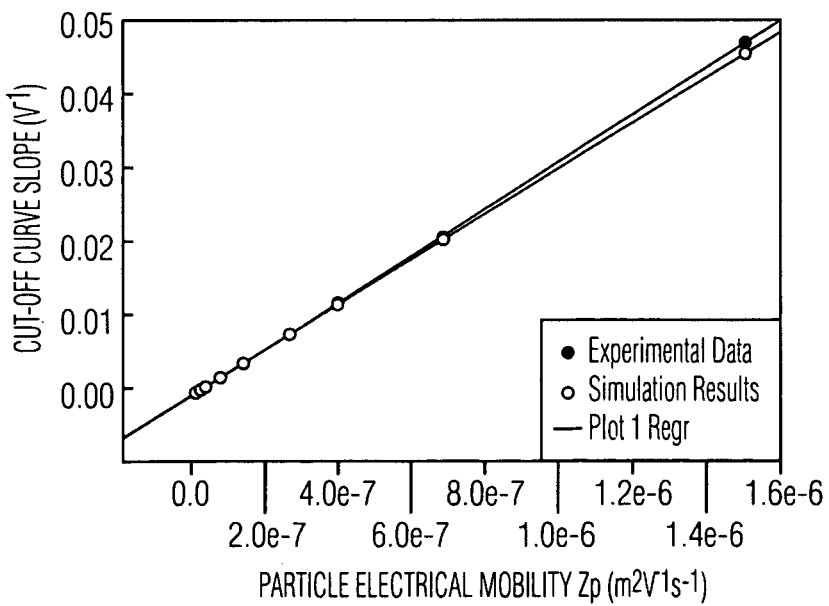

The total volume of the microscale differential mobility classifier 14 is about 3 cm$^3$. The characteristic cutoff curves displaying the percent penetration versus applied voltage for various particle sizes are shown in FIG. 4. This performance is shown in reduced coordinates of $Z_p$, the particle electrical mobility, in FIG. 5. A suitable example of the microscale differential mobility classifier 14 is a miniaturized disk-type electrostatic aerosol precipitator.

Referring back to FIG. 2, once the submicron-sized particles of a certain size of interest are isolated or separated in the sample separation section 200, the isolated submicron-sized particles are conveyed to the sample detection section 300 comprising a microscale particle counter 16. The microscale particle counter 16 is adapted to physically interact with the isolated submicron-sized particles passed from the microscale differential mobility classifier 14. This physical interaction with the isolated submicron-sized particle alters or deflects the physical structure of the microscale particle counter 16. From this deflection, a count signal can be generated therefrom.

Figure 10:
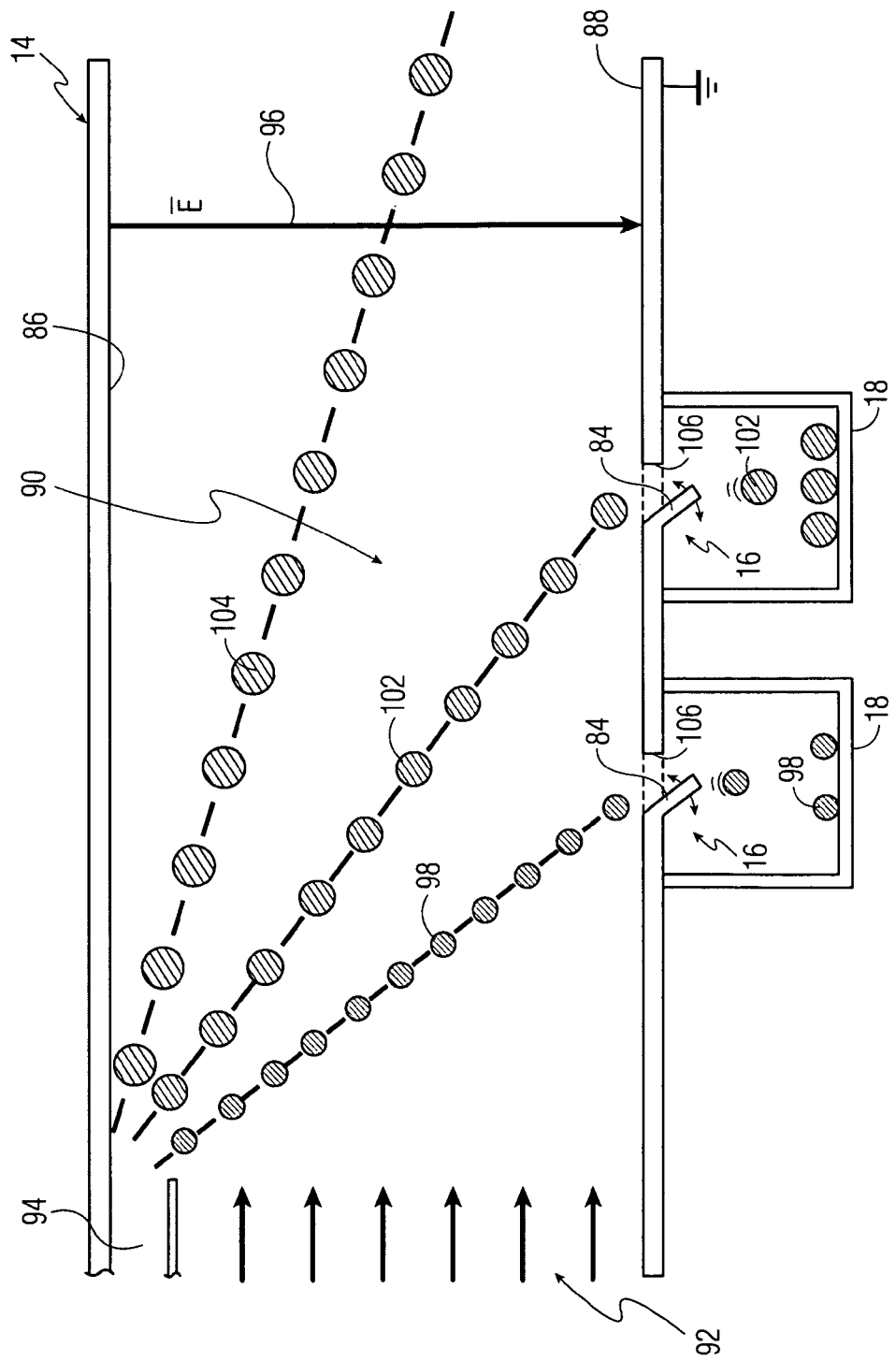

In one embodiment of the present invention, the microscale particle counter 16 includes one or more microscale cantilevers 84 (as shown in FIG. 10), each corresponding to a particular size or range of sizes, that can bend upon receiving thereon a load (i.e. submicron-sized particle). The cantilever 84 is a beam supported at one end by a fixed point or support, and can move from a first position to a second position when encountering a load or stress thereon. The cantilever 84 can be fabricated through micromachining techniques as known in the art of semiconductor fabrication technologies from any suitable material including, but not limited to, silicon, polymers, metals and the like. Preferably, the cantilever 84 is fabricated from silicon, silicon nitride or polymers. The fabrication process generally involves undercutting the cantilever structure to release it, often with an anisotropic wet or dry etching technique.

The microscale cantilevers 84 can be arranged in a spaced apart array to measure the number of submicron-sized particles for a range of sizes simultaneously. The deflection of the microscale cantilever 84 can be sensed through any means including discerning changes in the beam 84 as it bends including, but limited to, arrangement in space, electroresistive properties, vibrational resonance properties, optical properties, and the like. In another embodiment of the present invention, the microscale cantilever 84 can also be further adapted to measure the mass of the submicron-sized particles based on changes in natural or applied resonance frequency.

The count signal generated by the microscale particle counter 16 is communicated to the computer controller and analyzer 400, which is generally a personal computer loaded with a corresponding software program. The computer controller and analyzer 400 is used to scan the differential mobility classifier 14 through its size range, and record the resulting data stream from the microscale particle counter 16. The isolated and counted submicron-sized particles are passed from the microscale particle counter 16 into a corresponding particle holder 18 for subsequent testing or confirmation as will be further described hereinafter.

In a further embodiment of the present invention, it is desirable to separate in the sample separation section 200 of the sample material based on density corresponding to the particular agent, in addition to separating the sample material based on size as will be further discussed hereinafter.

Figure 6:
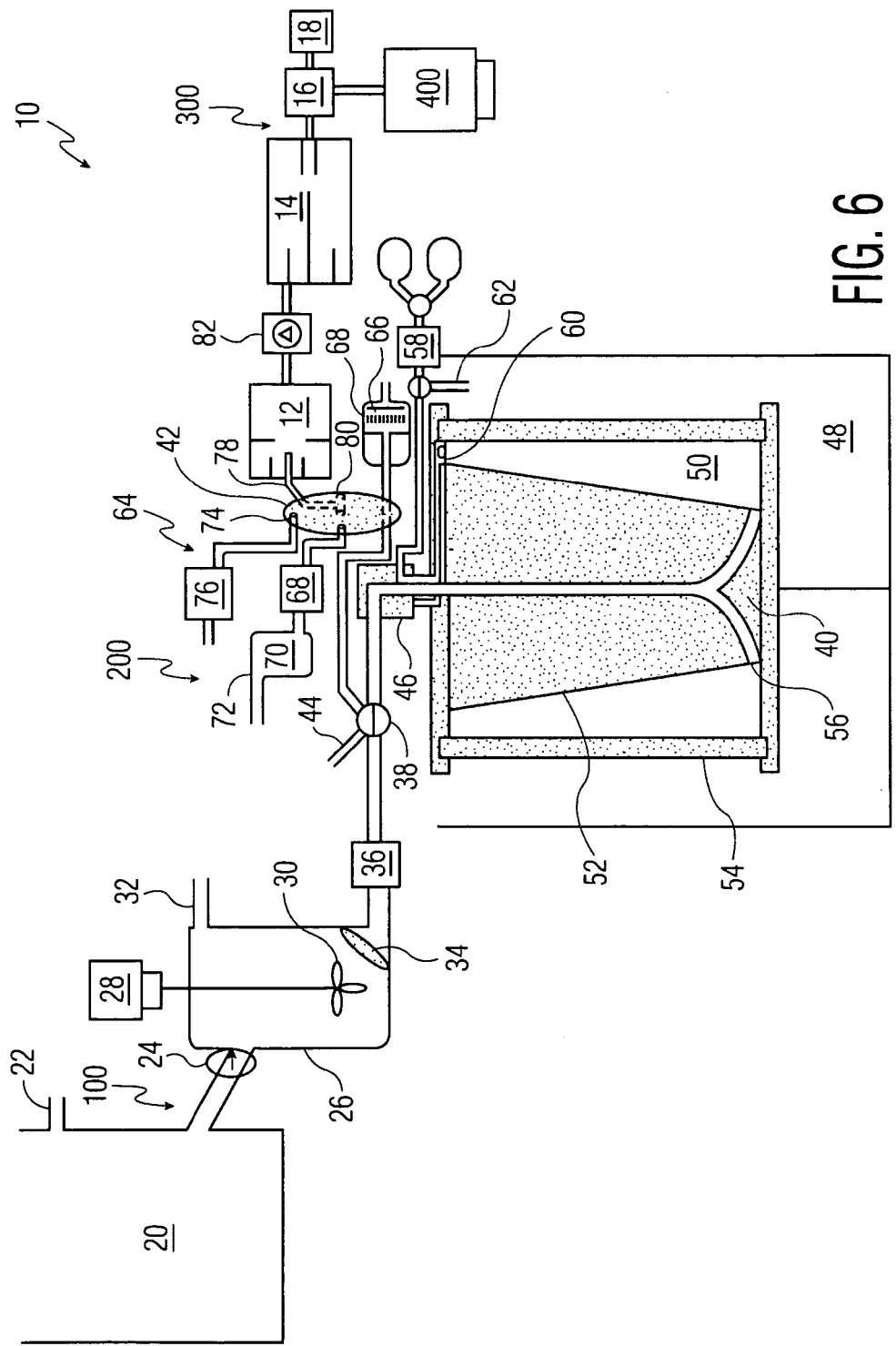

Referring to FIG. 6, the system 10 includes the sample collection section 100, the sample separation section 200, the sample detection section 300, and the computer controller and analyzer 400. The sample collection section 100 includes a collector 20 for aerosol or gaseous fluid sampling. The collector 20 is adapted to sample airborne particles in the approximate size range of from about 2 to about 10 microns and which may carry viruses and virus-like particles having a size range of from about 10 to about 1000 nanometers. Normal collection rates would be from about a hundred to several thousand liters/min of air. Collection of the submicron-sized virus particles in the collector 20 is facilitated by the fact that airborne viruses generally travel in or on aerosol particles, which measure larger than a micron. In exceptional cases where the virus is not rafting on a supermicron fomite, the danger of transmission by inhalation is generally reduced because of the distribution of submicron-sized particles in the atmosphere and the difficulty in capture by the lungs.

The collector 20 further includes a water inlet 22, which is connected to a water source, such as tap water or a water purification system. The collector 20 scrubs the collected particles with the incoming water from the water inlet 22. Examples of the collector 20 are the U.S. Army's XM2 or the SPINCON collector made by Midwest Research Institute of Kansas City, Mo.

In many applications other than aerosol sampling, samples, which may contain viruses, for example, are obtained without need for what would be considered a formal collection process, such as when the samples are already in the liquid form. These include, for example, blood samples, obtained by ordinary means familiar in clinical settings, as well as other body fluids such as mucus, semen, feces, lymph, saliva, and the like. Also in this category are situations involving sampling of bodies of water such as municipal water supplies, rivers and lakes, beverages, and high-purity water used for microelectronics manufacture.

The collector 20 further includes tubing 24, which connects the collector 20 to a holding tank 26 containing a blender or homogenizer 28. The collector 20 has an aqueous stream output on the order of 1 to 10 ml/minute containing the scrubbed particles which is pumped through the tubing 24, preferably of TEFLON or polysiloxane-coated to reduce adsorptive losses. The tubing 24 is connected to a one liter holding tank 26. Alternatively, the tubing 24 can be connected directly to the separation section 200.

In the holding tank 26, solids in the aqueous stream are broken up by using the homogenizer 28, or alternatively, by forcing the aqueous stream through an orifice. The homogenizer 28 has a bladed section 30. Surfactant or amphiphile is added at the inlet 32, which preferably is mixed with water prior to entry into the holding tank 26. The surfactant or amphiphile breaks down the structures in the aqueous stream. Preferably, the amphiphile has a low boiling point, which allows easy removal of the amphiphile in a later stage. Most preferred, the amphiphile is diethylene glycol monohexyl ether. Base is also preferably added to increase the pH of the homogenized liquid, which tends to decrease aggregation. Examples of the homogenizer 28 are the Lightnin Closed Tank Model general purpose stirrer model G2S05R, available from Lightnin, a unit of General Signal of Avon, N.Y., Catalog No. 869435, or the PC-controllable stirring motor, RE162 analog, ID No. 8000700 and rotor-stator S 50 N-W 65 SK, ID No. 8005100 from IKA Works, Inc. of Cincinnati, Ohio, which serves as part 30.

In leaving the holding tank 26, the aqueous stream passes a screen filter 34, which regulates the output of the holding tank 26. The screen filter 34 is preferably 10-micron mesh and made of stainless steel or other corrosion-free material. A pump 36, which is designed for pumping liquids through the tank 26, draws the aqueous stream from the holding tank 26 and through the screen filter 34.

Beyond the pump 36, a three-position PC-controlled switch 38 is used to allow the discharge from pump 36 to flow into a centrifuge rotor 40 in a first position. To understand the function of the second and third positions of this switch, it is necessary to realize that after centrifugation, the gradient imprisoned in the rotor can be divided into two parts: the useful part which contains that range (or in some cases, those ranges) of densities in which the particles to be detected are expected to lie, and the remainder which will generally be discarded and not sent on to the next stage. Thus, for example, in the detection of viruses pathogenic to humans, this useful part could be that part of the gradient corresponding to densities of 1.175 to 1.46 g/ml, as discussed elsewhere herein; alternatively, a subset of this range could constitute the useful range if only certain viruses are being analyzed for.

Thus, the second position of switch 38 allows the useful part of the gradient to flow on to part 42 (in particular, to the first position of part 42, as discussed below), and the third position of the switch allows the discarded portion of the gradient from the rotor 40 to flow out through a port 44; if desired, port 44 can incorporate means to recycle density gradient material, if desired. In the first position, as the screen-filtered sample from the pump 36 travels past the switch 38, it enters into the sample separation section 200.

In the sample separation section 200, the aqueous stream enters a liquid-cooled coaxial seal 46. After passing the coaxial seal 46, the aqueous stream enters at the upper shaft of the rotor 40. The rotor 40 is a zonal ultracentrifuge rotor, such as a Beckman's CF-32 rotor or Z-60 rotor, which is inserted into and spun by a centrifuge 48, such as a Beckman Optima XL-100K Preparative Ultracentrifuge. For large sample volumes with small quantities of viruses, for example monitoring of bodies of water, such as drinking water sources, the present invention preferably uses continuous-flow density gradient ultracentrifugation, using for example the Beckman's CF-32 rotor. For other applications, ordinary zonal centrifugation is preferred with rotor 40 being a Beckman's Z-60 rotor. In a special seal and bearing assembly, fluid inlet and outlet streams access an annular space 50 between a core 52 and rotor wall 54 through the coaxial seal assembly 46 and via port 56. Density gradient solutions, sample liquid, and the displacement fluid are sequentially pumped into the annular space 50. Density gradient solutions are loaded from port 58 through inlet 60. From the pump 36, sample liquid is added. A density gradient solution is any liquid, which permit the separation of viruses, such as a sucrose or, preferably, cesium chloride solution.

Figure 7:
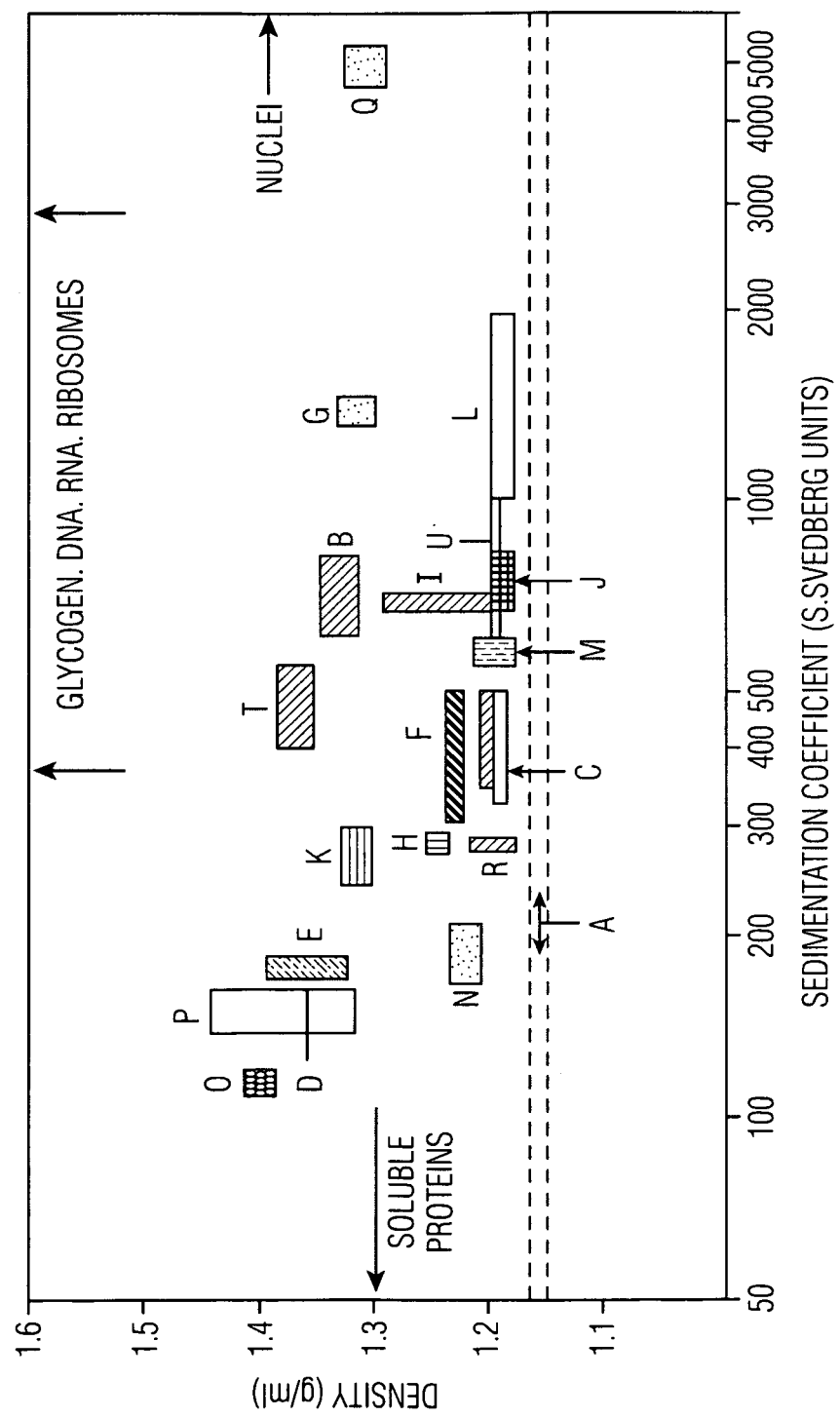

In continuous flow operation, the virus-containing liquid stream is pumped in from the sample collection section 100 and flows continuously over the density gradient in the rotor 40, and virus sediment out of the stream, banding into the density gradient according to buoyant density. This pumping of sample into and out of the rotor 40 can be performed with the centrifuge 48 spinning at high speed. The continuous stream allows a large volume of fluid to flow through the annular space 50, which permits virus material to be captured in the gradient, even with small concentrations of viruses in the fluid.

In ordinary zonal operation (not continuous-flow), the sample does not flow continuously into the rotor 40 for long periods of loading, but rather the entire sample volume, which must be less than the annular volume in the rotor 40, is loaded and enclosed in the rotor 40. The rotor volume is then closed off before acceleration to high speed. In either case, this is called the loading phase of the isopycnic banding separation. After loading and centrifuging to achieve banding, the virus-containing bands are recovered by displacing the bands sequentially, with lowest density bands exiting first and highest density last. As the density of each virus uniquely determines the position of that virus or particle in the exiting stream, the timing of the detection of specific virus particles provides particle density information.

A fresh gradient is loaded into the rotor 40 by pumping a low-density fluid, containing no cesium chloride, into the rotor 40. As illustrated schematically by the presence of two fluid tanks and a mixing valve in part 58 of FIG. 6, a high density fluid, typically containing about 60% cesium chloride is mixed with the low density fluid at a variable high:low ratio, which via PC control increases with time until the loading is complete. The fluids pass through the fluid entry ports 60 at the top of the annular space 50. Concurrently, the rotor 40 is spinning at a low speed of about 4,000 rpm, with the speed being controlled by the timer control system in tandem with the fluid entry and displacement.

After the fresh gradient is loaded, the control system actuates valves which flow fluid through the rotor 40 in the opposite direction, pumping sample from the holding tank 26, through switch 38 (in the first position), through the bottom entry port 56, and upward through the annular space 50, entering at the bottom end and displacing fluid out at the top of the rotor 40 through the fluid entry port 60 and out discharge port 62. After establishing flow reversal, the control system initiates and regulates the centrifuge to a preferred rotational speed of about 60,000 rpm for a B-series rotor. In extremely dry environments, water exiting the centrifuge may be recycled back into the system by pumping it back into the collector 20 where it can be used for air scrubbing. At a rotational rate of 60,000 rpm and flow rate as high as 6 liters/hr, over 90% of all viruses enters the gradient from the sample fluid stream, where it remains imprisoned. After on the order of 10 to 30 minutes of operation, which allows as much as 3 liters of sample fluid to pass through the rotor 40, the inflow and effluent flow are shut off, and the high-speed rotation continues for an additional 30 minutes to band the viruses. The viruses become banded in the gradient. The centrifuge controls are actuated by a timer-regulated control system, which is preferably a standard PC-computer interface.

In operation, sample liquid is introduced into the density gradient within the centrifuge rotor at the low-density end of the gradient, and each particle or molecule penetrates into the gradient at a rate that increases with the mass of the particle, and with the density. In the case of a protein molecule, the mass is much smaller than that of a virus by at least an order of magnitude, and the density is about the same as that of a relatively low-density virus. Accordingly, the rate of banding for proteins is much slower than for viruses. The centrifugation is run just long enough for the smallest virus particles of interest to have enough time to band to the desired resolution in the gradient. This is typically within about 1 to 5% of the equilibrium position. The proteins will then primarily be to the low-density side of their equilibrium positions, as they started on that side. Since the equilibrium position of most proteins in a gradient is nominally about 1.3 g/ml, at the end of this shortened operating time, most proteins are positioned considerably lower than 1.3. The proteins are at positions, which are not collected, and not sent on to the next stage as they are outside of the "virus window". Accordingly, the density-gradient centrifugation step takes on some of the properties of a combined two-stage density-gradient/sedimentation coefficient separation.

Once the viruses are banded, the centrifuge is decelerated to low speed, and the gradient is recovered by pumping the dense fluid of preferably 60% CsCl from the gradient supply system 58 to the outer edge of the annular space 50 through the fluid entry port 60. The dense fluid displaces the gradient, with low density bands exiting first followed by high-density bands. After gradient removal, the high-density material in the rotor 40 is displaced by low-density fluid, which enters from the inner rim of the annular space 50 at point 56 and displaces the high-density material from the outer edge of the annular space 50. The procedure is complete in a few minutes, and the cycle repeats again beginning with the loading of the density gradient at low speed.

Ultracentrifugation provides the advantages of desorption of viruses from fomites and universal capture of all catalogued and non-cataloged viruses, with high capture efficiencies of greater than 95%. Ultracentrifugation also is not dependent on biochemical reagents, and provides a high degree of virus separation from the background components. Additionally, density information of the viruses is provided by the ultracentrifugation, providing the y-coordinate in the Virus Window plot, discussed herein. The coaxial seal 46 is commercially available as a Beckman's Zone Assembly, Part No. 334241. Examples of the centrifuge rotor are the U.S. Army's B-VIII, B-IX and B-XVI, or preferably the Beckman Spinco CF-32 Ti Continuous Flow Rotor, or Beckman's Z-60 rotor for ordinary zonal centrifugation. For the centrifuge itself, the Beckman Optima XL-100K Preparative Ultracentrifuge is well suited for all of these rotors.

The results of the extraction of the ultracentrifugation of the centrifuge rotor 40 are analyzed from biological background by means of a "Virus Window". The Virus Window is a density-size (r-d) or density-sedimentation coefficient (r-S) plot of biological components which are pathogenic to humans, with the x-axis showing either size d or sedimentation coefficient S, and the y-axis showing density r, as shown in FIG. 7. FIG. 8 is a table providing the densities (g/ml) and size (nm) for known viral families containing species pathogenic to man. Most Mammalian viruses are approximately between 1.175 and 1.46 gm/ml density and have a diameter between about 22 and 200 nanometers (or, alternatively rephrasing this size range, with sedimentation coefficient between 120 and 6,000 Svedberg units). The Virus Window for plant viruses will be different.

The Virus Window of FIG. 7 is an extremely useful concept not only because it shows how viruses can be separated from other non-viral background, but also because the different virus families are substantially separable from each other. Within the Virus Window, each virus family is distinguished by a particular rectangle with little overlap between the 20 family rectangles. Accordingly, with a known density and size, the detected virus particle is pinpointed to its particular family in the Virus Window. In any case, particles with densities and sizes that both fall in the Virus Window ranges can, with high confidence, be presumed to be viruses; thus when counts are registered in the system 10 of the present invention, having previously been selected by centrifugation for density in the range of about 1.175 to 1.46, and further selected by the differential mobility classifier 14 for size between about 22 and 200 nm, then it can be concluded with a high degree of confidence that these indicate the presence of viruses in the sample.

Furthermore, this confidence level is further increased if the density and size fall into a particular region of the Virus Window known to correspond to a virus. Similarly, other particles of potential interest in detection—such as prions, other virus-like particles, and other natural or artificial particles, colloids, cell structures, or macromolecules—will frequently have unique positions in the density-size plot that may allow them to be separated from other components and thereby be detected in the system 10 of the present invention.

Although to a very large degree only pathogenic viruses fall within the Virus Window, other background components fall close to the Virus Window. These components are microsomes and similar sub-cellular structures. These components can be effectively eliminated by adding nonionic surfactant, such as diethylene glycol monohexyl ether, to the sample collection section 100 exit stream at inlet 32. The surfactant solubilizes the microsomes and membrane fragments. Where recovery of viable viruses is not necessary, release agents can be used. The release agents are preferably organic solvents and surfactants, more preferably amphiphiles, and most preferably low molecular weight amphiphiles such as diethylene glycol monohexyl ether. The release agents provide several useful effects.

First, they act to break up and even dissolve cellular substructures, such as microsomes, ribosomes, lysosomes, peroxisomes, and mitochondria, which have sizes and densities similar to viruses and set the limit on the required resolution, in the case of detection of viruses. Second, upon dissolution of the lipid envelope with such agents, the increase in the virus density is significant (the density of the viral core, which is the virus minus its lipid envelope, is in general significantly higher than that of the enveloped virus). In the case of hepadnaviridae, for example, this may be from about 1.25 to 1.36.

Both effects serve to further differentiate viruses from, particularly, microsomes in the Virus Window plot, the first by acting to eliminate the microsomes, and the second by increasing the difference in density between the viruses and the background microsomes. Third, release agents enhance the desorption of viruses from solid matter, which is particularly important in the detection of airborne viruses. Release agents can also break up aggregates of viruses, especially aggregates of encapsulated viruses. The present invention minimizes this aggregation problem in other ways besides the use of release agents. The centrifugation can be performed without pelleting.

Consequently, buoyant density, and thus isopycnic banding, is not greatly affected by aggregation under these circumstances. (Indeed, banding times are favorably reduced in the case of aggregation, and techniques can be applied that take advantage of this, within the broad context of the present invention). Any aggregation will generally produce only a small shift in, and/or broadening of, resulting virus bands. The portion of this exiting stream that contains the Virus Window is pumped to the sample separation section 200 with the position of a particle along this stream giving the density of that particle. The useful part of the stream, in the case of general virus detection where the range 1.175 to 1.46 is passed to the next stage, is in the preferred embodiment on the order of about 10 ml; thus, this section does not effect a large increase in virus concentration, though it does effect a very large increase in the concentration of viruses relative to other non-viral components.

Although feasible, a separate centrifugation to separate particles by sedimentation coefficient for Virus Window x-coordinate information is not necessary. The differential mobility classifier (DMC) 12, which is described below, provides rapid analysis of particle size. Additionally, separation of viruses from soluble proteins can also be done in the separation section 200. The centrifuge dimension and rotor speed for optimal centrifugation can be calculated. Optimal times are preferably thirty minutes or less and resolutions are preferably 0.02 density units (0.02 gm/ml) or better.

The sample fluid passes from the centrifuge 48 into a filtration portion 64 of the separation section 200. Typically, this could be in the form of 15 pulses, each on the order of 1-10 ml in volume, and each corresponding to a density slice with a width on the order of 0.02 gm/ml. In the filtration portion 64, a membrane filter 66 separates the viruses from soluble proteins (removing the need for a second, sedimentation rate centrifugation in the centrifuge 48), and concentrates particles with sizes greater than the pore size into a very small volume of liquid; additionally, in this stage soluble salts, including those from the sample as well as the density gradient material (e.g., cesium chloride), are greatly reduced in concentration. The membrane filter 66 may be Millipore's VIRESOLVE Membrane, an AMICON P membrane, or preferably a Pall FILTRON OMEGA Series membrane with a 1,000,000 molecular weight cutoff. The water permeability of the membrane filter 66 is on the order of 0.01 ml/cm$^2$-sec-psi, so that a membrane area of 0.1 cm$^2$ yields a flux of order 6 ml/min at 100-psig transmembrane pressure.

The membrane filter 66 is incorporated into a housing which is designed to allow flow rates on the order of 0.1 to 20 ml/min during filtration, which results in loading of the filter with particles larger than about 15 nm (which includes all virus particles), after which the particles are confined within a small front-face-side collection volume. A small-volume filtration filter holder 68, such as Schleicher & Schuell's SELECTRON, is used to hold the membrane filter 66. More preferably, a filter holder with a design like that of the SELECTRON, but made out of an alternative material which does not degrade electrolytically under high voltage, is used.

A four-way positioner 42 in the filtration portion 64 allows automated processing of particles in the membrane filter 66. The positioner 42 is driven by a computer-controlled motor, which positions the filter holder in one of four ports.

In the first position, the positioner 42 positions the membrane filter 66 to accept the sample flow outputted from the centrifuge 48. Each 0.02 gm/ml density slice from the output of the centrifuge 48 is, after passing through switch 38 in the second position, loaded through the membrane filter 66 in less than about 2 minutes; alternatively, larger density slices can be filtered, requiring appropriately longer times. A standard 0.2 micron pore size filter (such as available from Corning Costar) is preferably incorporated in the connection between the output from centrifuge 48 and the input to filtration portion 64, in order to remove any remaining particles greater than about 200 nm in size.

When the positioner 42 is switched to the second position, a valve closes off the sample flow and CsCl-free water from pump 68 out of tank 70 which has an inlet 72 is passed across the membrane filter 66 using on the order of 5 ml of water with a flux time of order 1 minute. This reduces the 30% CsCl aqueous solution surrounding the particles to less than 100 ppm CsCl, and allows recovery of the CsCl for recycling. Additionally, the amphiphile, viscosity additives and buffer components are reduced in the membrane filter 66. More preferably, ammonium acetate solution, with on the order of 20 mM concentration in water, is used for this operation, preparing the liquid for the downstream detection operation.

On switching the positioner 42 to the third position 74, the pure water (or ammonium acetate solution) is shut off, and a final filtration is performed in order to reduce the volume of liquid on the retentate side of the membrane, thereby greatly increasing the concentration of viruses and reducing the volume of liquid to the small quantities required for operation of the further size separation in the differential mobility classifier 14; the filtrate in this step passes out through port 76. More precisely, the filtration portion 64 is integrated with the compact field charger 12 by a punctured disk fitting. The fitting has a 150-micron hole drilled through a tubular stub in its center. When positioner 42 is in the third position, this hole allows the filtrate to pass out through port 76.

When the positioner 42 is in the fourth position, the inlet end of an electrospray capillary 78 (the end opposite the spray tip) of the compact field charger 12 is inserted into this 150-micron hole. This fits in a piston-like manner into the stainless steel cylinder of the SELECTRON (or SELECTRON-like) filter holder. The cylinder slides over the steel disk, and is positioned with a gap between the steel disk and the ultrafilter surface on the order of 100 microns.

In the fourth position 80, in accordance with the above, the membrane filter 66 is positioned for entry of the virus containing retentate into the electrospray capillary 78 of the compact field charger 12. (Alternatively, instead of fluid passing directly from the filtration portion 64 to the electrospray capillary 78, an intermediate component may be used to accomplish a further purification and/or concentration). A platinum wire may be run from the voltage source of the compact field charger 12 to the interior of the liquid inside the volume on the retentate side of the membrane filter, in order to establish a current return for the electrospray operation.

The compact field charger 12 and the differential mobility classifier 14 provide a final purification based on size of the submicron-sized particles. As discussed above, the size separation portion of the system 10 includes three major components; the microscale compact field charger 12, the microscale differential mobility classifier 14 and the microscale particle counter 16. The microscale compact field charger 12 and differential mobility classifier 14 units may be combined as a single integrated unit, which can be accompanied by an IBM PC with associated software. This allows for an inexpensive set up compared to a mass spectrometer. The detection section 300 can conduct measurements concurrently with the collector 20 obtaining the next cycle's collection.

Passing from the filtration portion 64, the retentate enters the size separation portion at the inlet of the electrospray capillary 78 of the compact field charger 12 in the fourth position of the positioner 42. Entry into the electrospray capillary 78 is done without passing the retentate through piping, which might cause sample losses. The electrospray capillary 78 is on the order of 25 cm in length, and the inlet of the electrospray capillary 78 is positioned to the small front-face-side collection volume of the UF membrane 66, as described above. The electrospray capillary 78 is then positioned to sample liquid from the retentate-side of the filter and the sample liquid enters the compact field charger 12.

In the compact field charger 12, the liquid sample solution is passed into an orifice or "jet" of 50-micron diameter, and droplets are ejected under the influence of an electric field. The droplets are typically between 0.1 and 0.3 microns in size, with a fairly narrow size distribution. At a droplet size of 0.3 micron, sampling rates are 50 nl/min (50 nanoliters/minute), allowing the compact field charger 12 to spray the collection volume in on the order of 20 minutes per microliter.

From the compact field charger 12, the sample passes to a charge neutralizer 82. The charge on the droplets is then rapidly recovered using an ionizing atmosphere to prevent Rayleigh disintegration. The neutralized charged droplets are then dried in flight, leaving the target virus molecules and/or dried residue of soluble impurities. From the charge neutralizer 82, the target virus molecules and/or dried residue enter the differential mobility classifier 14.

The differential mobility classifier 14 uses electrophoretic mobility of aerosol particles to classify the particles by size, using the inverse relationship between the mobility of a particle to its size. In the differential mobility classifier 14, particles are carried by an air stream at a set velocity through an electric field created by a charged rod. If the particle is singly and positively charged, it experiences an electrostatic attraction to the rod, which competes with the inertial force of the flow. When the electrophoretic mobility falls in a certain range, the particles pass through a narrow exit port at the end of the charged rod. The particle size range, which is generally 0.01 to 1 micron, is divided into 147 size channels. The entire range is automatically scanned in 1 to 10 minutes, generally 3 minutes. The differential classifier 14 has only a possible 3% instrumental error for virus size determination. Additionally, there is a possible size increase due to the covering of the virus particle with impurity residue, which at an impurity level of 100 ppm, a typical 40 nm virus has a possible error of up to about 2% in effective size. If the impurity levels are less than 20 ppm, the error becomes smaller than 1%.

When the primary droplets from the compact field charger 12 are 0.3 micron, a 1-ppm soluble impurity creates a 3 nm residue particle, and a 125-ppm soluble impurity creates a 15 nm particle. Particles, which are 15 nm in diameter, can be separated in the differential mobility classifier 14 from viruses, which are at least 22 nm in diameter. Accordingly, soluble impurities must be reduced to less than 100 ppm (0.01%) to avoid background interference with virus signals.

Detection of proteins at levels of $10^{11}$ to $10^{12}$ molecules/ml indicates that a sensitivity level for viruses of $10^{10}$ particles/ml can be achieved, and possibly $10^9$ particles/ml, particularly by combining the differential mobility classifier 14 selection with an adjustment of the Kelvin radius of approximately 10 nm. Impurities of 1 ppm yield a 3 nm residue particle, which can overlap protein sizes. Impurity levels of 100 ppm or less are acceptable in the detection of viruses, since viruses are several times larger than proteins. Sensitivities of $10^{10}$ molecules/ml and possibly $10^9$ molecules/ml are projected based on documented results using proteins.

The differential mobility classifier 14 validates against false positives by changing the dilution and seeing whether the particle size also changes. Additionally, the differential mobility classifier 14 can be used to provide another layer of protection against interference from impurities up to the 100-ppm level. The level of $10^{10}$ molecules/ml corresponds to $2\times10^7$ viruses in a 2-microliter-collection volume of the filtration portion 64, and $10^9$ molecules/ml correspond to $2\times10^6$ viruses. At a collection volume of $10^7$ viruses of the present invention, or minutes of XM2 sampling, 20,000 liters (20 m3) of air are sampled. Accordingly, the sensitivity of the system of the present invention is on the order of 500 viruses per liter of air. With impurity levels of 100 ppm or less, virus size can be determined by the differential mobility classifier 14 to within about 4%. The size separation portion requires on the order of 5 to 40 minutes, including the differential mobility classifier 14 size determination, and can be preformed concurrently with centrifugation for a subsequent cycle.

From the differential mobility classifier 14, the sample draws toward the microscale particle counter 16 forming part of the detection section 300. The aerosol sample sorted by the differential mobility classifier 14 contacts the cantilever 84 of the microscale particle counter 16 for receiving submicron-sized particles of a particular size or size range. The weight or momentum of the submicron-sized particle causes the cantilever 84 to deflect which allows the particle to pass therethrough. The deflection of the cantilever 84 is detected and a count signal is generated therefrom. The count signal is then recorded and analyzed via the computer controller and analyzer 400.

The filtration portion 64 has an output volumetric rate, which is very well suited for input into the microscale compact field charger 12, microscale differential mobility classifier 14 and the microscale particle counter 16, which addresses the strict requirements and narrow range of operating parameters for the overall unit. In recognizing the high value of this molecule-counting and molecule-sizing unit, filtration provides excellent samples for the size separation portion prior to detection.

The system 10 is controlled via the computer controller and analyzer 400. When data collection and instrument control are handled via the same computer, the computer may vary the mode of operation in response to virus detection. Initially, before viruses have been detected, the system 10 places the entire 300 ml of density gradient from the centrifuge 48 through the membrane filter 66 to scan all virus sizes from 22 to 200 nm. The differential mobility classifier 14 operates to indicate the sizes of the viruses detected. The computer can then trigger the output of the centrifuge 48 to be sampled piecewise in the filtration portion 64. By breaking the range of virus densities, which is about 0.3 gm/ml into 10 or 15 slices, the density of the detected virus is within about 0.02 to 0.03 gm/ml, which is sufficient to narrow most viruses down to a single family. Following this, the region in the centrifuge output stream surrounding this density can be divided still finer, to provide better accuracy on the viral density.

Through data base comparison, the system 10 identifies the viral families from the measured densities and sizes, and provides output of detected viruses by density, size, concentration, apparent changes in concentration over time, and if desired, audible and/or visual alarms in the presence of detected viruses. Being automated, the system 10 of the present invention can run continuously for long periods of time without an operator. In addition to making continuous virus monitoring possible at a large number of sites simultaneously without the need for scores of virologists, the automation afforded by the system 10 of the present invention also limits the risks of viral infection of technicians.

Other potential physical means of separating viruses and other particles from background and/or enriching their concentration may involve capillary electrophoresis (purification and concentration enrichment), sedimentation-rate centrifugation (primarily purification), hydroextraction (mainly concentration), dialysis (purification and concentration), organic/inorganic flocculation (purification and concentration), and capillary chromatography, which can size-exclusion, hydrophobic interaction, or ion-exchange chromatography (purification and concentration).

Figure 9:
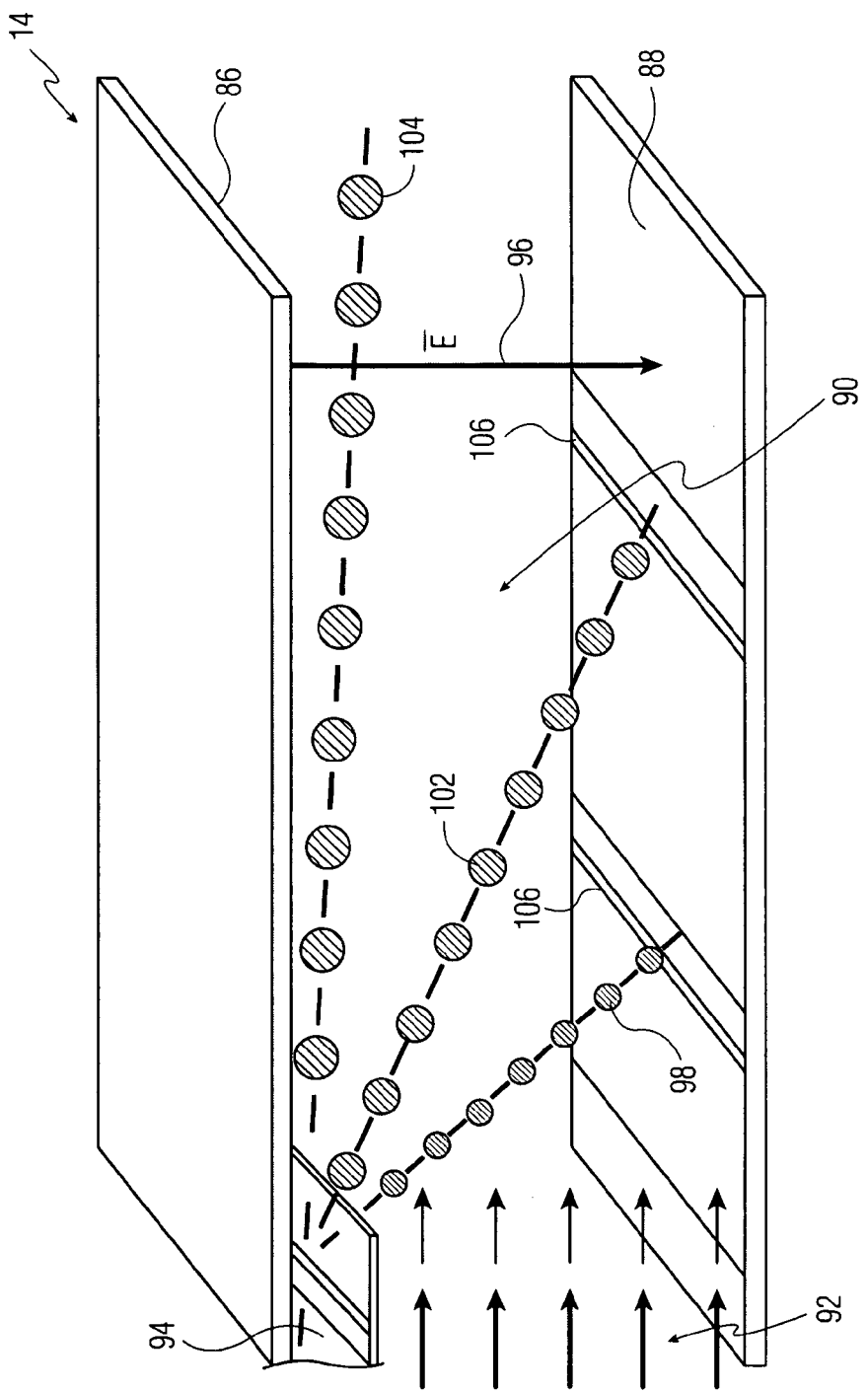

Referring to FIG. 9, a simplified representation of the microscale differential mobility classifier 14 is shown. As discussed above, the microscale compact field charger 12 generates a single charge on each of the submicron-sized particles prior to passage to the microscale differential mobility classifier 14. The microscale differential mobility classifier 14 receiving the charged submicron-sized particles separates the particles based on size as a function of electrical mobility. The microscale differential mobility classifier 14 operates on the basis that larger particles require more force to deflect than smaller ones.

The microscale differential classifier 14 includes a first inner surface 86, a second inner surface 88 parallel to the first inner surface 86, a space 90 defined by the first and second inner surfaces 86 and 88 with an air stream 92 flowing therethrough, and an inlet 94 for supplying the charged submicron-sized particles from the microscale compact field charger 12. The inlet 94 is positioned proximate the source of the air stream and the first inner surface 86. The first and second inner surfaces 86 and 88 are charged to produce an applied electric field 96 therebetween that causes the charged submicron-sized particles downward toward the second inner surface 88.

As the charged submicron-sized particles are introduced through the inlet 94, they become entrained in the air stream 92 moving horizontally from left to right. The intermediate submicron-sized particles 102 experience a greater rate of descent towards the second inner surface 88 than the larger submicron-sized particles 104 and lesser rate of descent than the smaller submicron-sized particles 98. In this manner, the submicron-sized particles are classified or segregated with each size hitting a specific location on the second inner surface 88. The microscale differential mobility classifier 14 further includes at least one aperture or opening 106 in the second inner surface 88 that is appropriately positioned downstream from the inlet 94 to receive submicron-sized particles of a corresponding size or range of sizes.

The size of the submicron-sized particles captured by the apertures 106 can be adjusted by modulating the strength of the applied electric field 96. When a relatively weak electric field 96 is applied, the larger particles 104 are able to overshoot the apertures 106 before hitting the second inner surface 88. As the strength of the applied electric field 96 is increased, the smallest particles 98 hit the second inner surface 88 before reaching an aperture 106, while the larger particles 102 and 104 travel the precise distance to fall through the apertures 106.

Referring to FIG. 10, a simplified representation of the microscale differential mobility classifier 14 integrated with the microscale particle counter 16 is shown. The apertures 106 in the second inner surface 88 each include a microscale particle counter 16 with a cantilever 84 positioned at the corresponding aperture 106. The cantilever 84 is deflectable from a first position to a second position to permit passage of the submicron-sized particles through the aperture 106. The system 10 further includes a particle holder 18 for collecting the separated and counted submicron-sized particles for subsequent testing or confirmation.

The corresponding deflection of the cantilever 84 produces a count signal via a suitable deflection detection means. Such deflection detection means can include, for example, a laser to track the movement of the cantilevers 84. Alternatively, the count signal can be generated based on changes in the natural resonant frequency of the cantilever 84 when a particle lands on the cantilever 84. The latter method can be used for precisely measuring the weight of the particle as it passes through the aperture 106. Since the microscale compact field charger 12 and the microscale differential mobility classifier 16 are extremely small, the number of particles passing through will also be small. The microscale particle counter 16 is sufficiently sensitive to effectively detect the passing of the particles, while maintaining the natural state of the particles for further testing.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A system for sampling and separating submicron-sized particles in an environmental sample, said system comprising:

means for collecting a sample suspected of containing submicron-sized particles from the environment, wherein said submicron-sized particles are in the size range of from about 5 to 1,000 nanometers;

means for separating the submicron-sized particles based on size into at least one size range, said means for separating the submicron-sized particles based on size receiving the submicron particles from said means for collecting a sample;

a microscale particle counter adapted for counting the size separated submicron-sized particles received from the means for separating the submicron-sized particles based on size, said particle, counter comprising at least one cantilever each corresponding to submicron-sized particles of a particular size range, said cantilever being deflectable from a first to a second position to permit passage of the submicron-sized particle therethrough, wherein the corresponding deflection of the cantilever generates a count signal; and a particle holder adapted for collecting and storing the submicron-sized particles passed by the cantilever.

2. The system of claim 1, wherein the cantilever is further adapted for measuring the mass of the submicron-sized particle prior to passage therethrough.

3. The system of claim 1, wherein the means for separating the submicron-sized particles based on size comprises:

a microscale compact field charger for placing a surface charge on the submicron sized particles; and a microscale differential mobility classifier receiving the charged submicron-sized particles from the compact field charger for separating the submicron-sized particles based on size as a junction of the electrical mobility.

4. The system of claim 3, wherein the microscale differential mobility classifier comprises:

a first inner surface;

a second inner surface parallel to the first inner surface;

said first and inner second surfaces defining a space having an air stream flowing therebetween;

an inlet for supplying the charged submicron-sized particles from the microscale compact field charger positioned proximate the source of the air stream and the first inner surface;

said first and second inner surfaces being charged to generate an electric field therebetween to cause the charged submicron-sized particles to move toward the second inner surface; and said second inner surface includes an aperture positioned at a sufficient distance downstream from inlet to receive a submicron-sized particle of a particular size, said aperture includes the microscale particle counter.

5. The system of claim 4, wherein the second inner surface includes one or more apertures located at varying distances from the inlet, wherein each aperture includes a corresponding microscale particle counter.

6. The system of claim 1, further comprising means for separating the submicron-sized particles based on density as a function of a density gradient, said means for separating the submicron-sized particles based on density receiving, the submicron-sized particles from the means for collecting a sample and then passing the submicron-sized particles to said means for separating the submicron-sized particles based on size.

7. The system of claim 6, wherein the means for separating the submicron particles based on density comprises an ultracentrifuge for initiating density-gradient ultracentrifugation of the sample so that the particles are banded according to density.

8. The system of claim 1, wherein the means for separating the submicron-sized particles based on size further comprises a filter apparatus for filtering the sample to purify and concentrate the submicron-sized particles.

9. The system of claim 1, wherein the means for collecting a sample comprises a collector having means for liquid scrubbing a collected sample of aerosol and gaseous materials containing the particles.

10. The system of claim 1, wherein the means for collecting a sample comprises an air sample collector.

11. The system of claim 1, wherein the submicron-sized particles are selected from the group consisting of viruses, prions, viral units, viral cores of delipidated viruses, plant viruses, portions of bacteria, and combinations thereof.

12. The system of claim 1, wherein the means for collecting a sample comprises a liquid sample collector.

* * * * *